(12) United States Patent
Lee et al.

(10) Patent No.: US 7,396,945 B1
(45) Date of Patent: Jul. 8, 2008

(54) METHOD OF PREPARING TETRAHYDROFURAN

(75) Inventors: Eun-Ku Lee, Kyonggi-do (KR); Yong-Ho Baek, Kyonggi-do (KR)

(73) Assignee: Hyosung Corporation, Kyonggi-do (KR)

( * ) Notice: Subject to any disclaimer, the term of this patent is extended or adjusted under 35 U.S.C. 154(b) by 0 days.

(21) Appl. No.: 11/785,654

(22) Filed: Apr. 19, 2007

(30) Foreign Application Priority Data

Feb. 16, 2007 (KR) .................. 10-2007-0016287

(51) Int. Cl.
*C07D 307/08* (2006.01)
(52) U.S. Cl. ............................ 549/509; 502/217
(58) Field of Classification Search .......... 549/509; 422/224; 502/217
See application file for complete search history.

(56) References Cited

U.S. PATENT DOCUMENTS

| 4,136,099 | A | 1/1979 | Smith |
| 4,665,205 | A | 5/1987 | Yamada et al. |
| 6,204,399 | B1 | 3/2001 | Schoedel et al. |

FOREIGN PATENT DOCUMENTS

| GB | 508548 | * | 7/1939 |
| JP | 61-126080 | | 6/1986 |
| JP | 9-59191 | | 3/1997 |

OTHER PUBLICATIONS

Castelnuovo et al., J. Therm. Anal. Cal., 2001, 233-247.*

* cited by examiner

*Primary Examiner*—Bernard Dentz
*Assistant Examiner*—David E Gallis
(74) *Attorney, Agent, or Firm*—Nixon & Vanderhye P.C.

(57) ABSTRACT

The present invention relates to a process for preparing tetrahydrofuran from 1,4-butanediol. According to the process in the present invention, a metal sulfate catalyst selected from the group consisting of aluminum sulfate, nickel sulfate, ferrous sulfate and chrome sulfate is pre-treated with an inert gas to be activated, followed by introducing into a reactor together with 1,4-butanediol.

5 Claims, 1 Drawing Sheet

METHOD OF PREPARING TETRAHYDROFURAN

TECHNICAL FIELD

Figure 1:
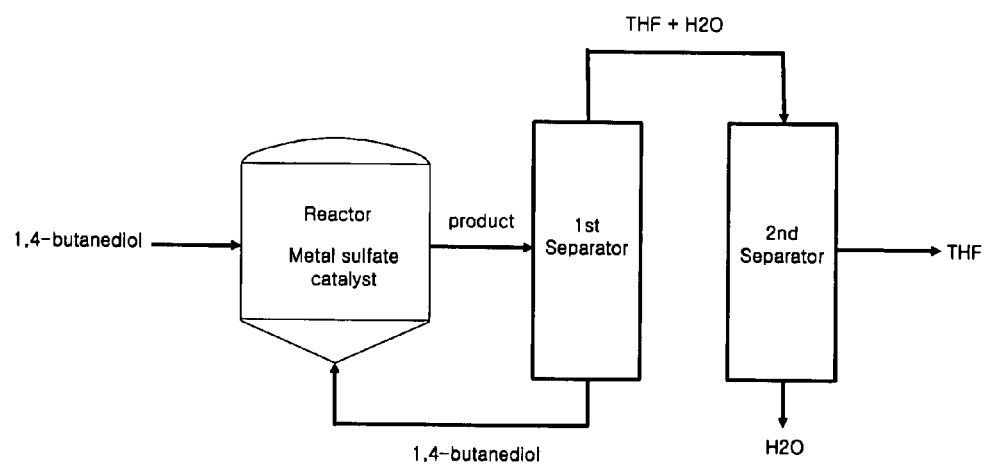

The present invention relates to a method of preparing tetrahydrofuran from 1,4-butanediol under the existence of a metal sulfate catalyst.

Tetrahydrofuran is widely used in various fields for solvent of organic compounds or synthesis material of polymers, etc. Recently its usage is growing for various kinds of polymer materials and additives.

Tetrahydrofuran can be prepared in various processes. According to the known arts, tetrahydrofuran is generally prepared by dehydrating 1,4-butanediol or by hydrogenating furan. According to the process of dehydrating 1,4-butanediol to prepare tetrahydrofuran, 1,4-butanediol is reacted under the existence of acidic catalysts, followed by separating moisture from the obtained tetrahydrofuran. The effectiveness of the process of preparing tetrahydrofuran depends on the performance of the acidic catalyst used in the reaction, thus it is all the more important to develop an efficient catalyst for the dehydration reaction of 1,4-butanediol.

BACKGROUND ART

A process of using inorganic acids such as sulfuric acid as a dehydration catalyst of 1,4-butanediol is disclosed in U.S. Pat. No. 4,665,205. However, by this process, the inorganic acid of catalyst is dangerous to use and causes a corrosion of equipments for reaction, thereby it being problematic.

Other catalysts for dehydration are, for example, an alumina catalyst as disclosed in U.S. Pat. No. 6,204,399; a silica-alumina catalyst as disclosed in JP-A No. H09-059191; a tungsten oxide catalyst supported on alumina as disclosed in U.S. Pat. No. 4,136,099; or a heteropoly acid catalyst as disclosed in JP-A No. S61-126080. Furthermore, it is a known method to use these acidic catalysts in the process of preparing tetrahydrofuran from 1,4-butanediol. However, these processes of dehydrating 1,4-butanediol have weak points relating to catalyst activity and stability.

Therefore, the present invention suggests a solution to problems of activity and stability of catalysts in known prior arts.

In order to solve the problems of low yield and a dangerous process of preparing tetrahydrofuran, it is an object of the present invention to provide a more safe and convenient process for preparing tetrahydrofuran.

DISCLOSURE OF THE INVENTION

According to a preferred embodiment of the present invention, after pre-treating a metal sulfate catalysts with inert gas to prepare an activated catalysts, they are used in the process of preparing tetrahydrofuran from 1,4-butanediol.

The metal sulfate, such as aluminum sulfate, nickel sulfate or chrome sulfate can be additionally introduced in quantities of 0.1 to 20 parts by weight, based on 100 parts by weight, of 1.4-butanediol.

According to a preferred embodiment of the present invention, an activation temperature of by pre-treatment is 150 to 350° C., and a reaction temperature of the reactor is 200 to 700° C.

According to a preferred embodiment of the present invention, the reactor can be fixed-bed reactor or mixed reactor.

According to a preferred embodiment of the present invention, the inert gas may be helium, nitrogen or argon gas.

Hereinafter, the present invention will be described in detail with reference to Examples. These Examples are provided only for the illustrative purpose, and it should not be construed that the scope of the invention is limited thereto.

According to the present invention, tetrahydrofuran may be prepared from 1,4-butanediol under the existence of the metal sulfate catalyst having a high efficient reaction activity. The metal sulfate catalyst used in the present invention shows excellent performances in its reaction activity, selectivity and stability. The metal sulfate catalyst may be used independently, or loaded on alumina, silica, titania or activated carbon.

The metal sulfate catalyst of the present invention may be a solid acid catalyst, and the acid strength and the kinds of the catalyst which represent the most important features of the metal sulfate catalyst, can be determined by catalyst precursor, the doping process of metal Sulfate and the catalyst activation process. In general, Lewis acid sites and BrØnsted acid sites may be co-existed on the surface of the metal sulfate catalyst, and these acid sites may produce a synergy effect by participating in the reaction.

The metal sulfate catalyst may be used in the reaction without a process of pre-treatment, but its catalytic activity may be increased when treated at 200 to 700° C. under the existence of inert gas such as hydrogen, nitrogen, helium or Argon. Moisture and impurities on the surface of catalyst are not efficiently removed under the temperature below 200° C., and at the temperature exceeding 700° C., the catalyst decomposition begins, as a result, lowering the reaction activity, thereby it being problematic.

Hereinafter, the process for preparing tetrahydrofuran in the present invention will be described in detail.

By using a fixed-bed reactor, metal sulfate catalyst fills a tubular reactor, and the catalyst is activated with the inert gas flown therein at 200 to 700° C. Furthermore, the catalyst is reacted with 1,4-butanediol along with the inert gas flown therein at a temperature of 150 to 350° C. and at a liquid hourly space velocity of 3 to 10 h$^{-1}$.

By using a mixed reactor, it is filled with 0.1 to 20 weight % of metal sulfate catalyst activated at 200 to 700° C. and 80 to 99.9 weight % of 1,4-butanediol, then heated at a temperature of 150 to 350° C. to initiate the reaction.

The temperature of the above-mentioned reaction may be 150 to 350° C., and especially, the reaction may occur more efficiently at a temperature of 200 to 270° C. While the reaction may not effectively carried out at a temperature below 150° C., the temperature over 350° C. may cause thermal decomposition of tetrahydrofuran, thereby lowering the selectivity. The process of the reaction is illustrated in FIG. 1.

Referring to the FIG. 1, the process for preparing tetrahydrofuran in accordance with the present invention is as follows.

As briefly illustrated in FIG. 1, 1,4-butanediol is introduced into a fixed-bed or mixed reactor filled with activated metal sulfate catalyst, followed by reacting for a certain amount of time in the reactor, as a result, 1,4-butanediol is converted to tetrahydrofuran. Products from the reactor comprise tetrahydrofuran, water and 1,4-butanediol, and among them the unreacted 1,4-butanediol is separated through the first separator, and recycled back to the reactor. Products from the first separator comprise tetrahydrofuran and water in the azeotropic state, the azeotropic mixture passes through the second separator, thereby a high purity tetrahydrofuran is obtained.

Hereinafter, the present invention will be described in detail with reference to Examples and Comparative Examples. These Examples are provided only for the illustrative purpose, and it should not be construed that the scope of the invention is limited thereto.

EXAMPLES

Example 1

A fixed-bed reactor with a diameter of 20 mm and length 520 mm was used to carry out a gas-phase catalyst reaction. The reactor was filled with 2 g of alumina sulfate catalyst first, and the catalyst was activated with helium gas at 370° C. for 2 hours. By using a syringe pump, 0.5 cc/min. of 1,4-butandiol was mixed with helium, and introduced into the reactor at a constant flow rate of 5.0 liter/h. The reaction was carried out at 200° C. under an atmospheric pressure, and the products as a result of the reaction were analyzed by on-line way using a Poropak QS column and a gas chromatography equipped with Flame Ionization Detector (FID). After the reaction was reached to the steady-state, products which passed through the reactor were analyzed. The yield of tetrahydrofuran was 98.5%.

Example 2

A liquid-phase catalyst reaction was carried out in 500 ml of three-necked round bottom reactor equipped with a magnetic agitator and a reflux. Prior to the reaction, the catalyst was activated using helium gas at 300° C. for 2 hours, and 0.5 g of the pre-treated aluminum sulfate and 100 g of 1,4-butandiol were introduced into the reactor. The reaction was carried out at the temperature of 200° C. for 1 hour, and the products from the reaction were condensed with a condenser. And then, the condensed products were distillated to separate remaining 1,4-butandiol, and analyzed using the gas chromatography as shown in Example 1. As a result, 98.5% of tetrahydrofuran was obtained.

Example 3 to 5

The process of preparing tetrahydrofuran was carried out in the same manner as shown in Example 2, except using 1 g of each transition metal sulfate catalyst such as nickel sulfate, ferrous sulfate and chrome sulfate and 100 g of 1,4-butandiol. Each yield resulting from the reactions is shown in Table 1.

Comparative Example 1 to 3

The process of preparing tetrahydrofuran was carried out in the same manner as shown in Example 2, except that 1 g of each of acidic alumina, tungstophosphoric acid which is a kind of heteropoly acid and silica alumina catalyst, and 100 g of 1,4-butandiol were used. Each yield resulting from the reactions is shown in Table 2.

TABLE 1

| | the yield according to the present invention | | | | |
|---|---|---|---|---|---|
| | Ex. 1 (fixed bed reactor) | Ex. 2 (mixed reactor) | Ex. 3 | Ex. 4 | Ex. 5 |
| catalyst | aluminum sulfate | aluminum sulfate | nickel sulfate | ferrous sulfate | chrome sulfate |
| yield (%) | 98.5 | 98.5 | 97.5 | 96.1 | 97.4 |

TABLE 2

| | the yield of comparative examples | | |
|---|---|---|---|
| | Comp. ex. 1 | Comp. ex. 2 | Comp. ex. 3 |
| catalyst | acidic alumina | tungstophosphoric acid | silica alumina |
| yield (%) | 76.1 | 83.4 | 73.2 |

As shown in Table 1, the results of reactions carried out in the fixed-bed and mixed reactor show the same yield. Among the tested metal sulfates, aluminum sulfate catalyst resulted in the highest yield of tetrahydrofuran. Comparing to the result shown in Table 2, however, all of yields in the table 1 are higher than those of the comparative catalysts. Though not shown in Table 1, nickel sulfate, ferrous sulfate or chrome sulfate was used to prepare tetrahydrofuran in the fixed-bed reactor, resulting in the same yield as in the case of the mixed reactor.

In the presented Examples, aluminum sulfate was used in quantities of 0.5 to 2.0 parts by weight based on 100 parts by weight of 1,4-butandiol, and each of nickel sulfate, ferrous sulfate and chrome sulfate were used in quantities of 1.0 part by weight. However, such amount of catalyst is not limited as shown in Examples, and it may be adjusted to various conditions like pre-treatment by the reaction condition or helium gas. However, it is preferable that metal sulfate is used in quantities of 0.1 to 20 parts by weight based on 100 parts by weight of 1.4-butandiol.

Under these conditions, when metal Sulfate is introduced to a process of reaction in the form of solid, it may realize a less dangerous process and prevent the corrosion of equipments for reaction. At the same time, tetrahydrofuran may be obtained in high yield as compared to using methods in the known arts.

EFFECTS OF INVENTION

The present invention enables a more convenient and less dangerous process of preparing tetrahydrofuran in high yield.

The invention claimed is:

1. The process for preparing tetrahydrofuran from 1,4-butanediol, comprising the steps of:
    pretreating a metal sulfate catalyst with an inert gas to be activated, and
    introducing the activated catalyst into a reactor with 1,4-butanediol wherein the metal sulfate catalyst is selected from the group consisting of aluminum sulfate, nickel sulfate, ferrous sulfate and chromium sulfate.

2. The process for preparing tetrahydrofuran from 1,4-butanediol according to claim 1, wherein the metal sulfate is introduced in quantities of 0.1 to 20 parts by weight based on 100 parts by weight of 1,4-butanediol.

3. The process for preparing tetrahydrofuran from 1,4-butanediol according to claim 1, wherein the temperature of activation by pre-treatment is 200 to 700° C., and the reaction temperature of the reactor is 150 to 350° C.

4. The process for preparing tetrahydrofuran from 1,4-butanediol according to claim 1, wherein the reactor is a fixed-bed reactor or a mixed reactor.

5. The process for preparing tetrahydrofuran from 1,4-butanediol according to claim 1, wherein the inert gas is selected from the group consisting of helium, nitrogen and argon gas.

* * * * *